United States Patent [19]
Moss

[11] Patent Number: 5,359,194
[45] Date of Patent: Oct. 25, 1994

[54] X-RAY CT MEASUREMENT OF SECONDARY (VUGULAR) POROSITY IN RESERVOIR CORE MATERIAL

[75] Inventor: Robert M. Moss, Houston, Tex.

[73] Assignee: Texaco Inc., White Plains, N.Y.

[21] Appl. No.: 123,672

[22] Filed: Sep. 20, 1993

Related U.S. Application Data

[63] Continuation-in-part of Ser. No. 877,512, May 1, 1992, abandoned.

[51] Int. Cl.$^5$ .................. G01N 23/087; G01V 5/00
[52] U.S. Cl. ........................ 250/255; 73/153; 378/4
[58] Field of Search ............ 250/253, 255; 378/4, 378/51, 53; 73/153

[56] References Cited

U.S. PATENT DOCUMENTS

| | | | |
|---|---|---|---|
| 4,722,095 | 1/1988 | Muegge et al. | 378/4 |
| 4,782,501 | 11/1988 | Dixon, Jr. | 378/4 |
| 4,799,382 | 1/1989 | Sprunt et al. | 73/153 |
| 4,868,751 | 9/1989 | Dogru et al. | 364/422 |
| 4,884,455 | 12/1989 | Vinegar et al. | 73/798 |
| 4,982,086 | 1/1991 | Withjack | 250/255 |
| 5,036,193 | 7/1991 | Davis, Jr. et al. | 250/255 |
| 5,048,328 | 9/1991 | Puri | 73/153 |
| 5,164,672 | 11/1992 | Gilliland et al. | 324/376 |

*Primary Examiner*—Constantine Hannaher
*Assistant Examiner*—Edward J. Glick
*Attorney, Agent, or Firm*—James L. Bailey; Kenneth R. Priem; Russell J. Egan

[57] ABSTRACT

A method for determining the secondary (Vugular) porosity of a reservoir core sample uses X-ray (CT) computed tomography to quantify the porosity. This is then compared with log derived secondary porosity and used to quantify secondary porosity heterogeneity in wells where no core samples are available.

6 Claims, 3 Drawing Sheets

Fig. 1A
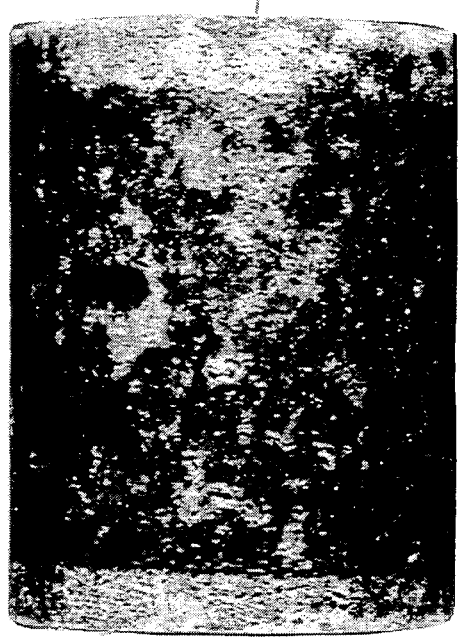
Fig. 1B
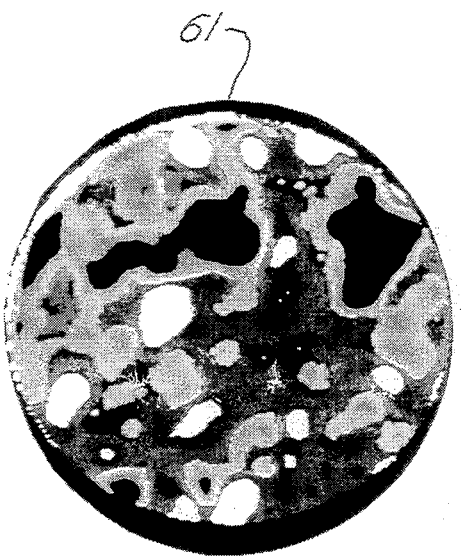
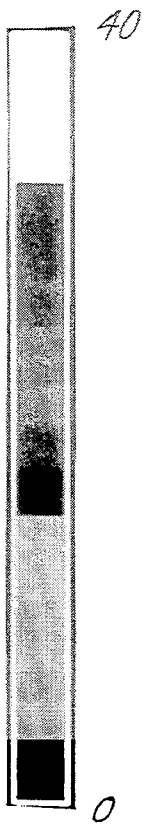
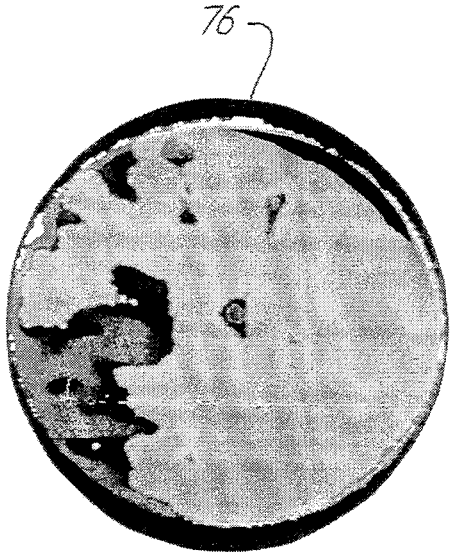
Fig. 2
Fig. 3

SECONDARY POROSITY CURVES
(POR2) & (POR2CT) FOR WELL "A"

X-RAY CT MEASUREMENT OF SECONDARY (VUGULAR) POROSITY IN RESERVOIR CORE MATERIAL

CROSS REFERENCE TO RELATED APPLICATION

The present application is a continuation in-part of my earlier patent application Ser. No. 07/877,512 filed May 1, 1992, now abandoned.

BACKGROUND OF THE INVENTION

1. The Field of the Invention

The present invention pertains to the use to X-ray computed tomography to measure the contribution of secondary (vugular) porosity to the overall pore volume in a reservoir sample.

2. The Prior Art

Previous methods to quantify vugular porosity in core material are limited to petrographic image analysis of thin sections. This has two well-known problems: (1) inherent inaccuracy due to the two dimensional nature of the measurement and (2) very limited sample volume. The present invention addresses both of these limitations by making a three dimensional measurement of the entire core volume.

Examples of prior art methods for examining earth cores may be found in U.S. Pat. Nos. 4,982,604; 5,036,193; and 5,058,425, the disclosures of which are incorporated herein by reference.

SUMMARY OF THE INVENTION

The present invention relates to a new technique to quantify secondary porosity using x-ray computed tomography (CT) of whole core samples. Sample cores from a heterogeneous limestone-dolomite formation with water production problems were used to develop this invention. Identification of secondary porosity heterogeneity by CT agreed well with core descriptions and well log results.

Secondary porosity, as measured by the difference between log derived density-neutron porosity and sonic porosity, was correlated with the CT data to establish the validity of the subject method. The log-derived secondary porosity showed good agreement with the quantitative, whole core CT data and core descriptions. Previous attempts to correlate log-derived secondary porosity with core data relied on thin section measurements.

The goal of this invention is to use x-ray computed tomography to quantify the secondary porosity heterogeneity. Conformation of the CT results with log data and by direct measurements allows confidence in using log measurements to quantify secondary porosity hetrogenuity in wells where no core sample is available.

BRIEF DESCRIPTION OF THE DRAWINGS

"The file of this patent contains at least one drawing executed in color to meet the requirements of 35 U.S.C. 112. Copies of this patent with color drawing(s) will be provided by the Patent and Trademark Office upon request and payment of necessary fee."

The present invention will now be described, by way of example, with reference to the accompanying drawings in which:

FIGS. 1A+B which shows photos of two core plugs from well "A" in a limestone-dolomite reservoir, plug "61" showing high secondary porosity and plug "76" showing predominately intercrystalline porosity;

FIG. 2 is a CT porosity image of a slice from plug "61" showing high secondary porosity (white areas);

FIG. 3 is a CT porosity image of a slice from plug "76" showing primarily intercrystalline porosity;

DETAILED DESCRIPTION OF THE PRESENT INVENTION

Figure 4:
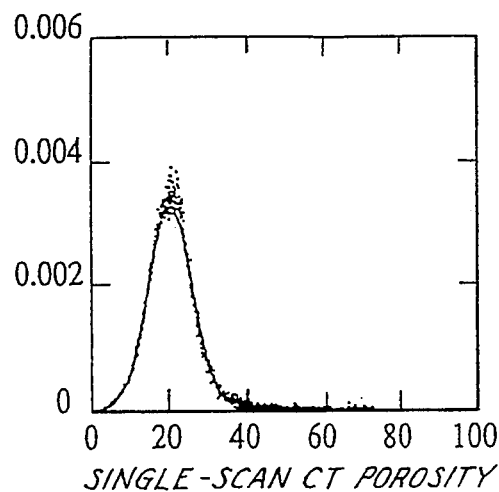
FIG. 4 is a graph of single scan CT porosity near plug 61.

The present invention concerns a method for determining the contribution of secondary (vugular) porosity to the total pore volume of a core sample. The present invention comprises the following steps:

(1) A plurality of CT scans are taken of a core of earthen material. The material can be scanned in either an "as received" native state (at ambient temperature and pressure conditions) or in a confined state, i.e. in a core barrel under confining stresses similar to those the core would have experienced in the reservoir.

(2) The scanned images are then transferred from the CT scanner to an image analysis computer for processing.

(3) ACT number image from the image analysis computer, which is displayed in Hounsfield Units (HU), is translated into an estimated porosity image. The equation that relates porosity to the CT number image is given below:

$$H_c = (1-\phi)*H_r + \phi*(S_f*H_f + S_g*H_g)$$

where
$H_c$ = CT number (Hounsfield Units) of the core
$H_r$ = CT number of the zero porosity rock matrix
$\phi$ = core porosity
$H_g$ = CT Number of the gas in the core
$H_f$ = CT Number of the fluid in the core
$S_f$ and $S_g$ = the fractional saturations of the fluid and the gas in the core, respectively.

The fluid in the core is used in the equations above since, in their native state, brine and oil have nearly the same CT number. A more general equation can be used, if necessary, no separate the fluid into both brine and oil contributions.

In general, to do this estimate with only a single set of scans, assumptions must be made about gas and fluid saturations of the core. For native state cores, being fluid-filled is a reasonable assumption ($S_f = 1$) while for cleaned, dried cores, being gas-filled is a reasonable assumption ($S_g = 1$).

The value for $H_r$ can be calculated theoretically from a presumed or known mineralogy, estimated from the CT data, or calculated by comparing measured CT numbers with independently measured porosity data from the same areas of the sample.

(4) After converting the CT number image to a porosity image, a region of interest within the porosity image is selected to create a porosity histogram of the porosity distribution within that region or portion of the porosity image. The porosity histogram is normalized to one pore volume.

(5) The shape of the porosity histogram for a relatively homogeneous core having secondary porosity generally can be described as a peak caused by the intergranular matrix component and a broad scattering of high porosity areas that are a result of the vugular porosity (vugs will have very high local porosity). A gaussian distribution is fit to the peak in the porosity histogram caused by the matrix component. For core material that has a relatively homogeneous mineralogy, the gaussian distribution will be a good approximation to the peak in the porosity histogram.

(6) The gaussian distribution that describes the peak in the porosity histogram has both a mean and a standard deviation (which is an estimate of the amount of local variability of the porosity within the image). The secondary porosity is now defined as any areas of the image whose porosity is more than three standard deviations above the mean of the gaussian distribution. The three standard deviation cutoff gives a high confidence level that the secondary porosity, as we have defined it, is not a part of the gaussian distribution which describes the intergranular matrix porosity.

(7) The contribution to the pore volume from the secondary porosity (vugs) is the ratio of the area under the (normalized) porosity histogram that has been identified as secondary porosity to the total area under the porosity histogram. This secondary porosity distribution is made up of a range of pore sizes significantly larger than that of the primary pore system.

This method has been confirmed by directly measuring the secondary porosity using a dual scan CT method, and by correlation of log-derived secondary porosity with the CT measured secondary porosity using the above method.

Figure 5:
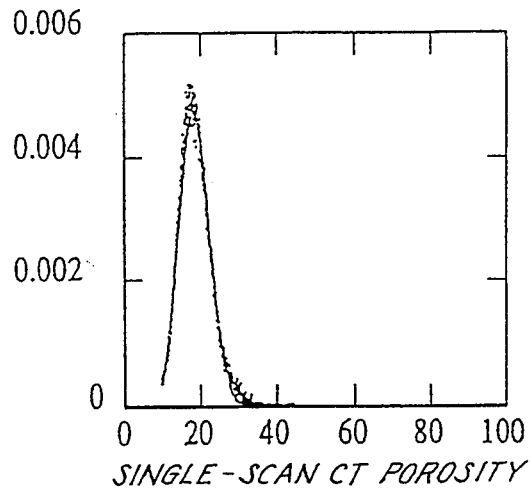
FIG. 5 is a graph of single scan CT porosity near plug 76.

The single-scan secondary porosity data have a voxel size of 0.25 mm×0.25 mm×2.0 mm=0.125 mm$^3$ in FIGS. 4 and 5. FIG. 4 shows a Fit Mean of 20.3; a Fit RMSD of 5.8; an SP Cutoff of 37.6; a % SP of 3.5 and a Mean SP of 52.2. FIG. 5 shows a Fit Mean of 18.3; a Fit RMSD of 4.1; an SP Cutoff of 30.5; a % SP of 1.1 and a Mean SP of 33.4.

For the dual-scan xenon injection studies of well "A", which directly measured the porosity distribution, each voxel 0.16 mm×0.16 mm×2 mm=0.051 mm$^3$. This volume is only about 40% of the volume in the single-scan data reported for this well. The voxel size should be kept in mind when comparing xenon and single-scan porosity data. Many of the differences between the histograms of the two types of data reflect differences in the heterogeneity of the samples at the two scales.

The porosity distributions of two representative areas from well "A" are shown in FIGS. 4 and 5. The solid line is a gaussian fit to the matrix peak. These histograms are normalized to one pore volume. Areas of the distribution above the cutoff for secondary porosity are shown shaded.

In order to confirm the results of the single-scan analysis, the porosity of eight representative core plugs from well "A" was measured directly. To perform the direct porosity measurement, the evacuated plug samples were scanned, flooded with xenon gas, and re-scanned at the same locations. The evacuated images were subtracted from the xenon images and scaled to produce porosity images:

$$\phi = \frac{CTN_{ROCK+Xe} - CTN_{ROCK+VACUUM}}{CTN_{Xe} - CTN_{VACUUM}} \quad (6)$$

where CTN=CT number. The values for the denominator in equation 6 were obtained by separate measurements made at various xenon gas pressures using the same apparatus.

Figure 7:
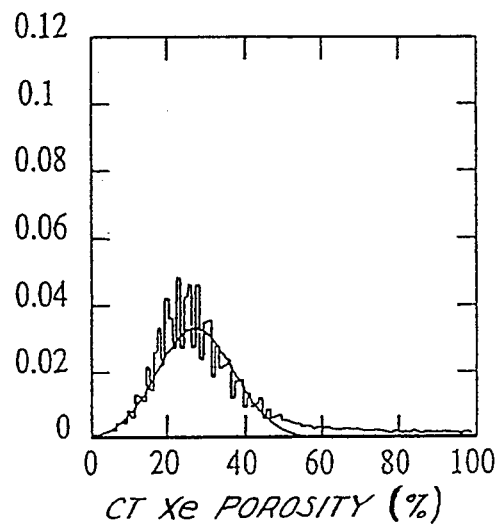
FIG. 7 is a graph of CT Xe porosity for plug 61.
Figure 8:
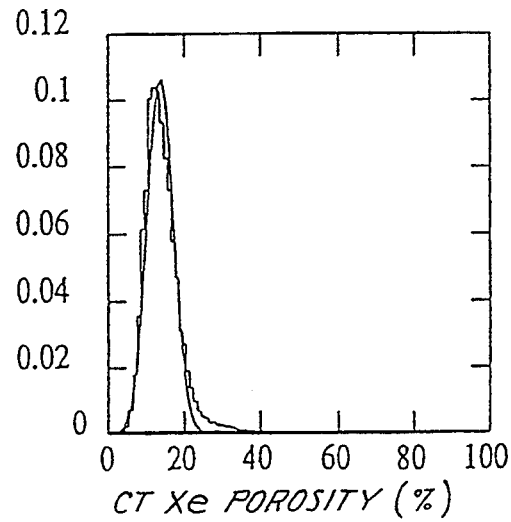
FIG. 8 is a graph of CT Xe porosity for plug 76.
Figure 6:
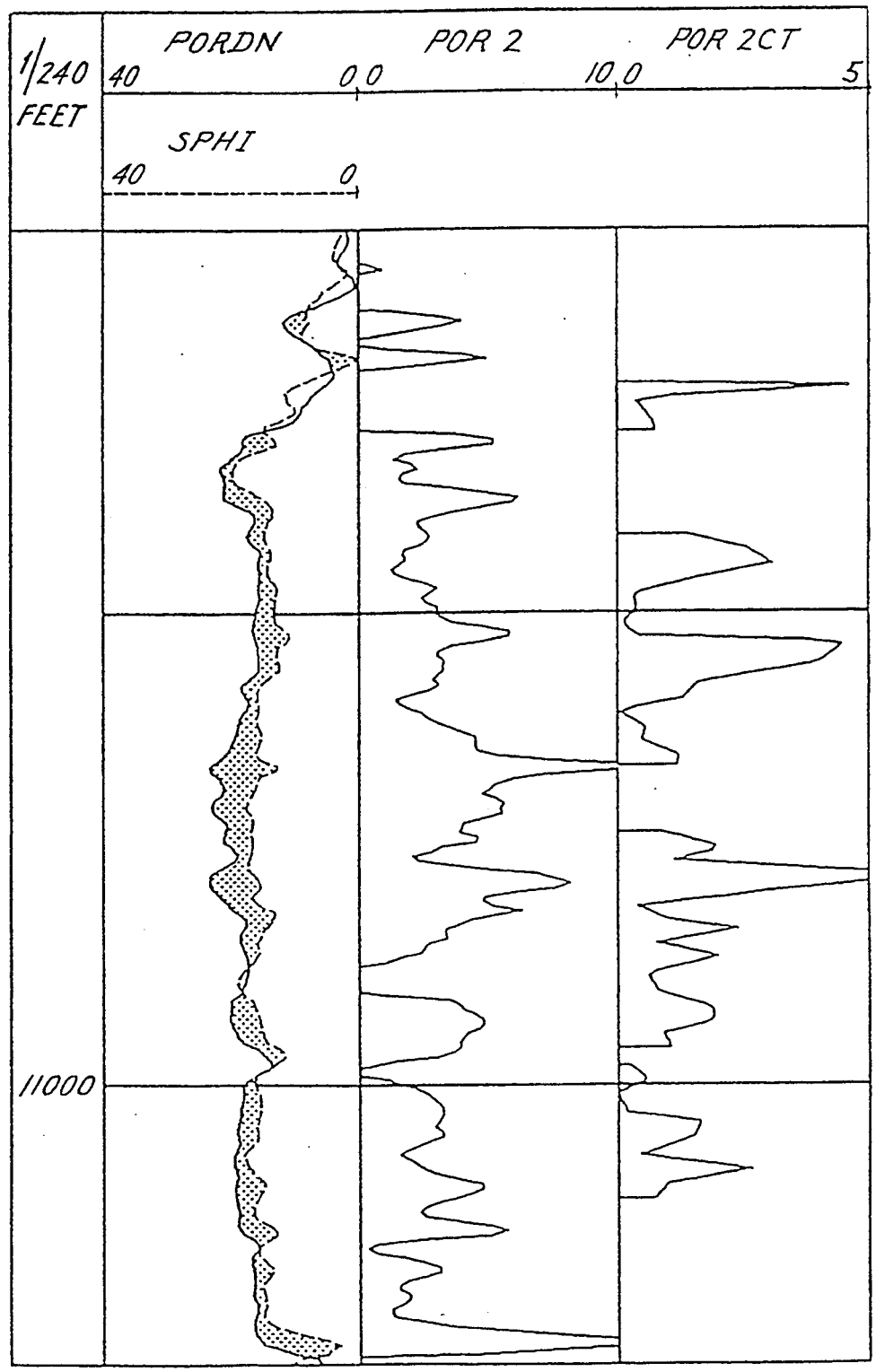
FIG. 6 is a graph of secondary porosity curves.

The porosity distributions for two of the plugs studied are shown as porosity histograms in FIG. 7 and 8. FIG. 7 shows an XeCal of 6.6; a Mean of 32.1; an RMSD of 17.4; a Fit Mean of 27.3; a Fit RMSD of 9.9; an SP Cutoff of 56.9: a % SP of 9.4 and a Mean SP of 74.9. FIG. 8 shows an XeCal of 14.4; a Mean of 14.2; an RMSD of 4.7; a Fit Mean of 13.7; a Fit RMSD of 3.4; an SP Cutoff of 23.9; a % SP of 4.0 and a Mean SP of 28.6. These distributions are normalized to one pore volume. The best gaussian fit to the data is shown with a solid curve.

Most of the relevant statistics from both the single-scan and xenon data for these samples are compared in Table I. Note in particular the good agreement between the single-scan estimate for mean porosity and the directly measured mean porosity is a result of the extended high porosity tail of these distributions. The porosity of the peak of the distributions, i.e. the most probable porosity value, agrees well with the single scan estimate for the mean porosity. Some of the differences between the amounts of secondary porosity present, as well as the mean values of the secondary porosity, are due to the smaller voxel size for the dual-scan data. These differences are telling us something about the scale of the heterogeneity within the samples. For example, the mean value for the secondary porosity for plug 61 is large compared to the single-scan data because the voxel size for the xenon measurement was smaller than the larger pores. For a sample where the results for secondary porosity are almost the same, e.g. plug 76, one might deduce that the relevant pores are all significantly smaller than a voxel, so that no difference is observed.

The general shapes and values from the direct measurement of the porosity distributions are in excellent agreement with the porosity distributions estimated from the single-scan data (FIGS. 4,5,7 and 8). The highest permeability plugs (plug 61, FIG. 7) show by far the largest standard deviations, and the most secondary porosity. These samples have some vugular pores which are larger than the voxel size (0.051 mm$^3$).

In general, the direct measurements have confirmed the assumptions made concerning mineralogy in the single-scan study, thus validating the results of the single-scan study for well "A".

Correlating the CT-derived secondary porosity to well logs is essential in predicting porosity heterogeneity where no core exists. Verification of log-derived secondary porosity typically comes from visual core observations or scatterted thin sections. The successful correlation of quantitative whole core CT data with log derived values increases confidence in using logs to identify secondary porosity in the reservoir.

Secondary porosity can be quantified using single-scan x-ray computed tomography. This was verified by direct, dual-scan measurements of porosity distributions using xenon injection. The use of whole core gives a more complete, unbiased measurement of secondary porosity than thin sections.

Log-derived secondary porosity shows good agreement with quantitative CT data and core descriptions. This provides confidence that logs can be used to identify secondary porosity heterogeneities in this reservoir.

The present invention may be subject to many changes and variations without departing from the spirit or essential characteristics thereof. The above described embodiment should therefor be considered in all respects as being illustrative and not restrictive of the scope of the invention as defined by the appended claims.

TABLE I

| | | Single-Scan and Xe Porosities Well "A" | | | | | | | | |
|---|---|---|---|---|---|---|---|---|---|---|
| | | SINGLE SCAN DATA | | | | DUAL SCAN (Xe) DATA | | | | PLUG DATA |
| PLUG | DEPTH (ft) | SS PHI | RM SD | % SP | MSP | Xe PHI | RM SD | % SP | MSP | He PHI |
| 40 | 10955.1 | 17.0 | 5.22 | 4.6 | 28.0 | 17.4 | 5.7 | 4.4 | 38.5 | 17.9 |
| 59 | 10979.8 | 13.7 | 5.42 | 6.3 | 46.5 | 25.3 | 12.5 | 9.7 | 79.6 | 18.9 |
| 61 | 10984.1 | 20.3 | 5.79 | 3.1 | 53.5 | 27.3 | 9.9 | 9.4 | 74.9 | 24.1 |
| 72 | | | | | | 24.2 | 4.3 | 5.1 | 51.2 | 23.8 |
| 73 | 10993.8 | 19.3 | 5.5 | 1.9 | 45.7 | 17.7 | 5.6 | 7.3 | 55.4 | 19.2 |
| 74 | 10995.3 | 19.1 | 6.0 | 1.9 | 48.7 | 18.9 | 4.5 | 3.3 | 36.4 | 17.9 |
| 76 | 10996.5 | 18.3 | 4.0 | 0.9 | 35.6 | 13.7 | 3.4 | 4.0 | 28.6 | 15.0 |
| 83 | 11005.0 | 18.9 | 4.23 | 0.2 | 34.7 | 17.5 | 5.3 | 13.7 | 43.5 | 17.1 |

TABLE I LEGEND
PLUG Plug number for xenon study, from DEPTH interval.
DEPTH depth of the top of the dataset internal (ft).
SS PHI mean of fit to single-scan CT porosity for interval.
RMSD standard deviation of matrix porosity fit.
% SP percentage of secondary porosity in the pore volume
MEAN SP(MSP) mean secondary porosity (%)
He PHI core plug porosity (%)
Xe PHI mean of fit to Xe CT porosity for plug matrix

I claim:

1. A method for measuring the fractional contribution of secondary porosity in reservoir core material from X-ray CT measurements, comprising the steps of:
providing an earthen core;
providing an X-ray computed tomography (CT) scanner for scanning said core and generating signals corresponding to each scan;
scanning said core and generating said signals;
transferring the signals from the CT scanner to an image analysis computer for processing;
translating a CT number image from said image analysis computer, in Hounsfield Units (HU), into an estimated porosity image using an equation that relates porosity to the CT number image as given below;

$$H_c = (1-\phi)^* H_r + \phi^*(S_f^* H_f + S_g^* H_g)$$

where
$H_c$ = CT number (Hounsfield Units) of the core
$H_r$ = CT number of the zero porosity rock matrix
$\phi$ = core porosity
$H_f$ = CT number of the fluid in the core
$H_g$ = CT number of the gas in the core
$S_f$ and $S_g$ = the fractional saturations of the fluid and the gas in the core, respectively;
selecting a region of interest within the estimated porosity image to create a porosity histogram of the porosity distribution within that region;
describing a gaussian distribution the shape of which approximates the peak of the porosity histogram caused by the intragranular matrix component of said earthen core;
fitting the described gaussian distribution to said peak and indentifying the secondary porosity as any areas of the porosity histogram whose porosity is more than three standard deviations above the mean of the fitted gaussian distribution; and
defining the fractional contribution of secondary porosity to the total pore volume as a ratio of the area under the porosity histogram that has been identified as secondary porosity to the total area under the porosity histogram.

2. A method according to claim 1 wherein said earthen core is scanned under ambient temperature and pressure conditions.

3. A method according to claim 1 wherein said earthen core is contained in a core barrel and scanned in a confined state under reservoir conditions.

4. A method according to claim 1 wherein said earthen core is assumed to be fluid filled.

5. A method according to claim 1 wherein said earthen core is assumed to be gas filled.

6. A method according to claim 1 wherein said histogram is normalized to one pore volume.

* * * * *